(12) United States Patent
Kim et al.

(10) Patent No.: US 11,518,735 B2
(45) Date of Patent: Dec. 6, 2022

(54) PSEUDOCERAMIDE COMPOUND WITH IMPROVED STABILITY AND COMPOSITION COMPRISING SAME

(71) Applicant: AE KYUNG INDUSTRIAL CO., LTD, Seoul (KR)

(72) Inventors: Han Young Kim, Daejeon (KR); Yu Mi Kim, Daejeon (KR); Hye Jin Hyun, Daejeon (KR)

(73) Assignee: AE KYUNG INDUSTRIAL CO., LTD., Seoul (KR)

( * ) Notice: Subject to any disclaimer, the term of this patent is extended or adjusted under 35 U.S.C. 154(b) by 247 days.

(21) Appl. No.: 16/765,832

(22) PCT Filed: Nov. 20, 2018

(86) PCT No.: PCT/KR2018/014269
§ 371 (c)(1),
(2) Date: May 20, 2020

(87) PCT Pub. No.: WO2019/103433
PCT Pub. Date: May 31, 2019

(65) Prior Publication Data
US 2020/0354309 A1    Nov. 12, 2020

(30) Foreign Application Priority Data

Nov. 27, 2017   (KR) ........................ 10-2017-0159680

(51) Int. Cl.
*A61K 8/68* (2006.01)
*C07C 233/09* (2006.01)
*A61Q 5/12* (2006.01)
*A61Q 19/00* (2006.01)

(52) U.S. Cl.
CPC .............. *C07C 233/09* (2013.01); *A61Q 5/12* (2013.01); *A61Q 19/007* (2013.01)

(58) Field of Classification Search
CPC ....... A61Q 19/00; A61Q 19/007; A61Q 5/002
See application file for complete search history.

(56) References Cited

U.S. PATENT DOCUMENTS

2011/0059157 A1    3/2011   Awasthi

FOREIGN PATENT DOCUMENTS

| CN | 1602181 A | 3/2005 |
| CN | 104854081 A | 8/2015 |
| CN | 107108470 A | 8/2017 |
| KR | 20110059157 A | 6/2011 |
| KR | 20130030093 A | 3/2013 |
| KR | 20130128737 A | 11/2013 |
| KR | 20160057760 A | 5/2016 |
| KR | 101641702 B1 * | 7/2016 |
| KR | 20170103359 A | 9/2017 |
| KR | 101878491 B1 | 7/2018 |

OTHER PUBLICATIONS

International Search Report and Written Opinion and English Translation for PCT/KR2018/014269; dated Feb. 27, 2019; 9 pages.

* cited by examiner

*Primary Examiner* — Qiuwen Mi
(74) *Attorney, Agent, or Firm* — Schwabe, Williamson & Wyatt, PC

(57) ABSTRACT

The present disclosure relates to a novel pseudoceramide compound. More specifically, the present disclosure provides: a novel pseudoceramide compound represented by Formula 1, having skin moisturizing and barrier function restoring characteristics; and a composition for an externally-applied dermal preparation, the composition containing the novel pseudoceramide compound.

9 Claims, 3 Drawing Sheets

PSEUDOCERAMIDE COMPOUND WITH IMPROVED STABILITY AND COMPOSITION COMPRISING SAME

CROSS-REFERENCE TO RELATED APPLICATION

The present application is a national phase entry under 35 U.S.C. § 371 of International Application No. PCT/KR2018/014269, filed Nov. 20, 2018, which designates the United States of America, which claims priority to KR Application No. 10-2017-0159680, filed Nov. 27, 2017, the entire disclosures of each of these applications are hereby incorporated by reference in their entireties and for all purposes.

TECHNICAL FIELD

The present disclosure relates to a pseudoceramide compound having skin protecting and moisturizing, barrier function recovering characteristics and a hair moisturizing effect, and a composition comprising the pseudoceramide compound and having skin moisturizing and barrier function recovery characteristics. In addition, the present disclosure relates to a compound having improved stability, which is devised for research into various formulations.

BACKGROUND ART

The skin stratum corneum is quite an important structure for moisture retaining and protecting functions of the skin. Specifically, intercorneocytic lipids form an interkeratinocytic lamellar structure to function like hard cement, which may lead to a skin barrier function basis. The intercorneocytic lipids comprise lipid components, such as ceramides, cholesterol, fatty acids, etc. and, inter alia, ceramides are the most pivotal lipids in the intercorneocytic lipids so as to be contained in the amount of approximately 50% by weight based on the total weight of the intercorneocytic lipids and exert a skin barrier function.

In addition, ceramides constitute lamellar liquid crystalline structures together with cholesterol, fatty acids to form a robust structure offering a skin barrier function. Therefore, impairments in ceramides may weaken a skin barrier function, thereby leading to adverse effects on intrinsic functions of the skin, and resulting in various skin troubles or diseases, such as atopic dermatitis, etc., or aggregating symptoms of the skin troubles or diseases.

In addition, ceramides constituting intercellular lipids are also present in the hair. The stratum corneum of the skin and the cuticle of the hair perform similar functions. The hair cuticle, which is present in the outermost part of the hair, prevents the hair from being damaged and functions as a barrier for protecting the hair from external stimuli. The ceramides exist in the hair cuticles and perform functions of strengthening and protecting internal tissues of the hair.

As ceramides are known to be essential, many cosmetic companies and pharmaceutical companies are focusing on researches for development of products using ceramides. However, since it is practically difficult to obtain naturally occurring ceramides, pseudoceramide compounds, which are structurally and functionally substantially the same with ceramides present in the skin, are being developed. Ceramides currently being applied in Korea on a commercial basis include ceramides extracted from microorganisms (natural ceramides), a pseudoceramide compound developed and manufactured by Amore Pacific Corporation (Korea) under the trade name PC-104 (International Patent Publication No. WO2014-084676), pseudoceramide developed and manufactured by the present applicant under the trade name PC-9S (U.S. Pat. No. 6,221,371), etc. However, existing pseudoceramide compounds are restricted in general purpose use due to a cost problem arising because of a complicated manufacturing process. Ceramides may have another drawback of being insoluble due to their structural characteristics.

Accordingly, it is highly required to conduct researches into materials of new pseudoceramide, which can be easily prepared to enable general purpose uses, and have improved solubility.

DESCRIPTION OF EMBODIMENTS

Technical Problem

To solve the problems, the present disclosure provides a novel pseudoceramide compound with improved stability, which has skin protecting/moisturizing and barrier function recovery characteristics.

The present disclosure also provides a skin-moisturizing externally-applied dermal preparation composition as a lipid component exerting a skin barrier function to offer high affinity to the skin and an excellent moisture retaining capacity.

The present disclosure also provides a hair cosmetic composition which can protect the hair, increase binding forces of internal hair tissues, regenerate the hair and exert a hair protecting function.

In addition, the present disclosure provides a compound having improved stability by devising a compound structure enabling research into various formulations.

Solution to Problem

To achieve the above and other objects, in an aspect of the present disclosure, there is provided a compound represented by Formula 1:

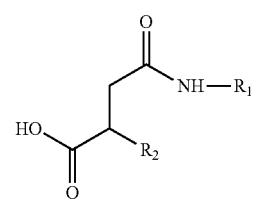

[Formula 1]

wherein $R_1$ represents a saturated linear C8-C18 alkyl group, and $R_2$ represents an unsaturated linear C4-C22 alkyl group.

The compound having a pseudoceramide structure represented by Formula 1 is prepared by a one-step reaction between a succinic acid derivative and alkyl amine.

An example of the compound having a pseudoceramide structure represented by Formula 1 may be a compound represented by Formula 2:

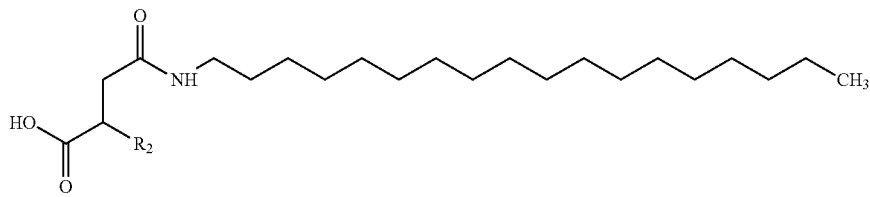

[Formula 2]

wherein $R_2$ represents an unsaturated linear C4-C22 alkyl group.

In another aspect of the present disclosure, there is provided a skin-moisturizing externally-applied dermal preparation composition comprising the pseudoceramide compound. The skin-moisturizing externally-applied dermal preparation composition may be formulated into one or more selected from the group consisting of a cream, an essence, a lotion, a toner, a gel, and an ointment.

In still another aspect of the present disclosure, there is provided a hair cosmetic composition comprising the pseudoceramide compound, the hair cosmetic composition being formulated into a shampoo or a hair essence.

Advantageous Effects of Disclosure

As described above, according to the present disclosure, the novel compound having a pseudoceramide structure is structurally and functionally similar to ceramides present in the skin and can be easily prepared, thereby enabling general purpose use. In addition, a solubility problem can be solved by devising the compound to have an asymmetrical structure.

In addition, the novel compound having a pseudoceramide structure according to the present disclosure can be applied to various kinds of cosmetic formulations as well as to the skin externally-applied dermal preparation composition that can be used as a moisturizer by forming a structure exerting a skin barrier function.

Furthermore, the novel compound having a pseudoceramide structure according to the present disclosure can also be applied to various hair cosmetic compositions by protecting the hair, increasing binding forces of internal hair tissues, regenerating the hair and exerting a hair protecting function.

In addition, the solubility issue can be addressed by devising the compound having an asymmetrical structure. In addition, the compound of the present disclosure has improved thermal solubility, thereby enabling research into various formulations.

BEST MODE

Figure 1:
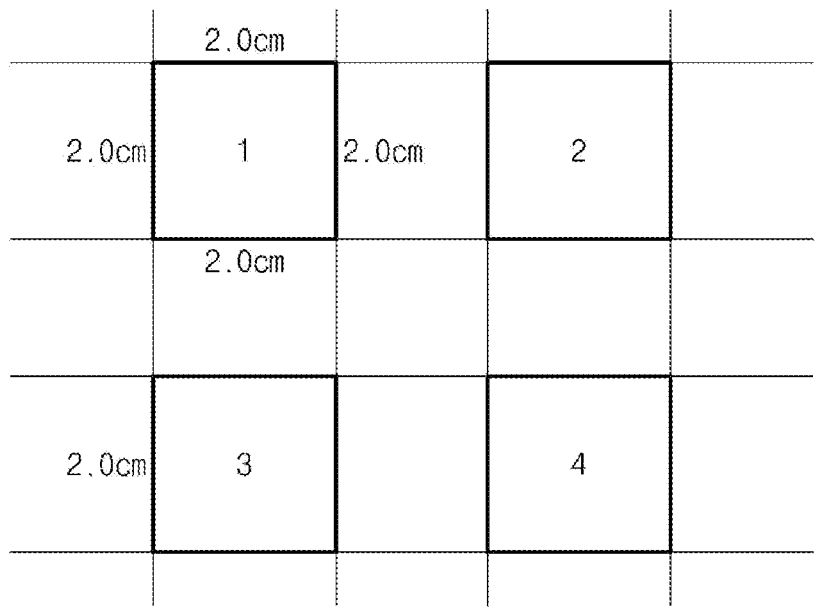
FIG. 1 illustrates body parts from which moisturizing capacities of a moisturizing lotion prepared in Experimental Example 1 of the present disclosure are measured.

Hereinafter, the present disclosure will be described in detail, such that those skilled in the art can easily practice the present disclosure.

The present disclosure provides a novel pseudoceramide compound represented by Formula 1, having skin moisturizing and barrier function restoring characteristics:

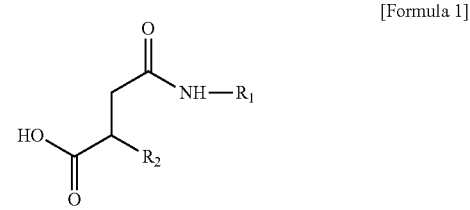

[Formula 1]

wherein $R_1$ represents a saturated linear C8-C18 alkyl group, and $R_2$ represents an unsaturated linear C4-C22 alkyl group.

The present invention relates to synthesis of pseudoceramides structurally similar to ceramides, which are primary lipids for a skin barrier function and are found in the skin and is embodied based on a sphingosine structure. The compound represented by Formula 1 is a new compound, which is easily prepared through a reaction between a succinic acid derivative and alkyl amine and enables general purpose use. More specifically, the present invention provides a novel pseudoceramide compound as a lipid component essential for a skin barrier function to offer high affinity to the skin and an excellent moisture retaining capacity through a ring-opening reaction between a succinic anhydride derivative and alkyl amine.

In addition, in order to increase solubility of the pseudoceramide compound, the pseudoceramide compound is asymmetrically structured by varying lengths of alkyl groups.

It was experimentally confirmed that when the alkyl chain in $R_1$, of two alkyl chains contained in the developed compound, had a double bond, the compound exhibited poor thermal stability. It was also confirmed that the compound had decomposition rates varying depending on the temperature and the decomposition of the compound was accelerated when the temperature become higher.

According to an embodiment, of two alkyl chains contained in the developed compound, the alkyl chain in $R_2$ preferably has only one double bond.

The novel compound of Formula 1 having the pseudo-ceramide structure of the present disclosure comprises a compound represented by Formula 2:

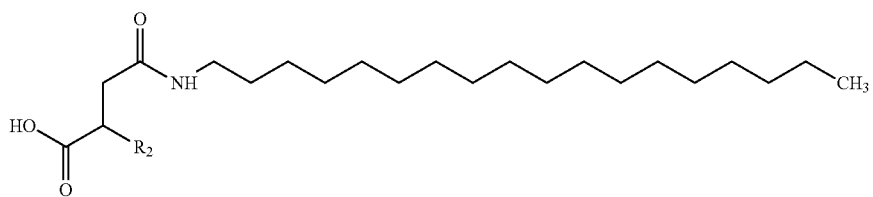

[Formula 2]

wherein $R_2$ represents an unsaturated linear C4-C22 alkyl group.

The novel compounds having the pseudoceramide compounds of Formulas 1 and 2 are synthesized through a ring-opening reaction between a succinic anhydride derivative and alkyl amine.

According to Examples of the present disclosure, examples of the novel compound having the pseudoceramide structure of Formula 1 may include a compound of Formula 3:

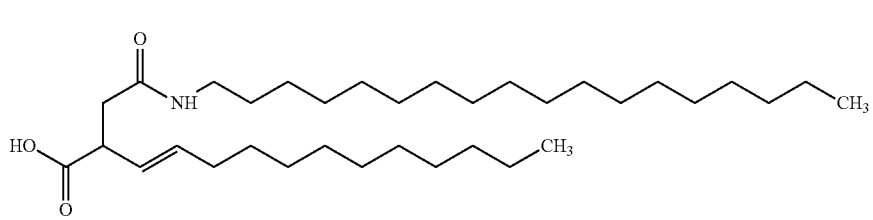

[Formula 3]

wherein stearyl amine was used as an amine group and was obtained by a ring-opening reaction with succinic anhydride of C12 having at least one double bond.

According to Examples of the present disclosure, examples of the novel compound having the pseudoceramide structure represented by Formula 1 may include a compound represented by Formula 4:

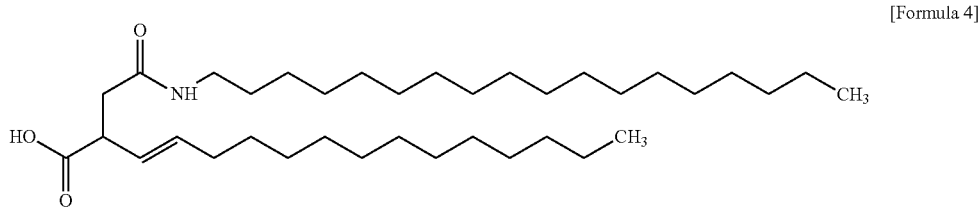 [SMILES: CCCCCCCCCCCC/C=C/C(CC(=O)NCCCCCCCCCCCCCCCCCC)C(=O)O]

[Formula 4]

wherein stearyl amine was used as an amine group and was obtained by a ring-opening reaction with succinic anhydride of C14 having at least one double bond.

According to Examples of the present disclosure, examples of the novel compound having the pseudoceramide structure represented by Formula 1 may include a compound represented by Formula 5:

[Formula 5]

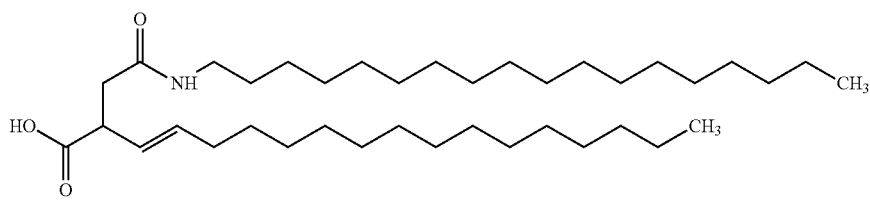

wherein stearyl amine was used as an amine group and was obtained by a ring-opening reaction with succinic anhydride of C16 having at least one double bond.

According to Examples of the present disclosure, examples of the novel compound having the pseudoceramide structure represented by Formula 1 may include a compound represented by Formula 6:

[Formula 6]

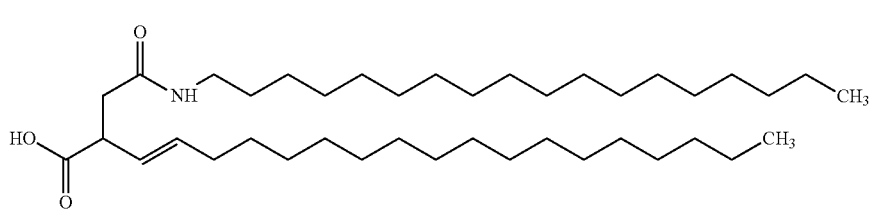

wherein stearyl amine was used as an amine group and was obtained by a ring-opening reaction with succinic anhydride of C18 having at least one double bond.

The novel pseudoceramide compound according to the present disclosure, which is represented by Formula 1, is prepared by mixing succinic anhydride and stearylamine in a weight ratio of 1:0.5 to 2 and stirring the mixture for 10 to 60 minutes. A solvent that can be used for the reaction may include dichloromethane, chloroform and toluene, and dichloromethane is most preferred.

The novel pseudoceramide compound according to the present disclosure may be used generally alone or in combination with other functional components in an amount of 0.0001 to 10.0 wt %, preferably 0.0005 to 10.0 wt %, and more preferably 0.005 to 10% wt %, based on the total weight of the cosmetic composition.

When used for a medical topical composition, the novel pseudoceramide compound according to the present disclosure may be used in an amount of 0.1 to 10 wt % and preferably 0.4 to 2.0 wt %, based on the total weight of the topical composition.

The cosmetic composition of the present disclosure may further include one or more compositions selected from the group consisting of a water-soluble vitamin, an oil-soluble vitamin, a high-molecular peptide, a high-molecular polysaccharide, and a sphingolipid.

The water-soluble vitamin may be used without limitation as long as it can be blended with cosmetics. Preferably, the water-soluble vitamin may include vitamin B1, vitamin B2, vitamin B6, pyridoxin, pyridoxine hydrochloride, vitamin B12, pantothenic acid, nicotinic acid, nicotinic acid amide, folic acid, vitamin C, or vitamin H. Also, salts (thiamine hydrochloride, ascorbate sodium, etc.) or derivatives (ascorbic acid-2-phosphate sodium, ascorbic acid-2-phosphate magnesium, etc.) of the above-described components may be included in the water-soluble vitamin which may be used in the present disclosure. The water-soluble vitamin may be obtained using a conventional method such as microbial transformation, purification from a culture solution of a microorganism, enzymatic or chemical synthesis.

The oil-soluble vitamin may be used without limitation as long as it can be blended with cosmetics. Preferably, the oil-soluble vitamin may include vitamin A, carotin, vitamin D2, vitamin D3, vitamin E (dl-α tocopherol, d-α tocopherol) and the like. Also, derivatives of the above-described components (ascorbic acid palmitate, ascorbic acid stearate, ascorbic acid dipalmitate, acetic acid dl-α tocopherol, nicotinic acid dl-α tocopherol vitamin E, DL-pantothenyl alcohol, D-pantothenyl alcohol, pantothenyl ethyl ether, etc.) are included in the oil-soluble vitamin which may be used in the present disclosure. The oil-soluble vitamin may be obtained using a conventional method such as microbial transformation, purification from a culture solution of a microorganism, enzymatic or chemical synthesis.

The high-molecular peptide may be used without limitation as long as it can be blended with cosmetics. Preferably, the high-molecular peptide may include collagen, hydrolyzed collagen, gelatin, elastin, hydrolyzed elastin, keratin, etc. The high-molecular peptide may be obtained in a purified form using a conventional method such as purification from a culture solution of a microorganism, enzymatic or chemical synthesis, or be purified from a conventional natural source such as thick skin from pigs or cattle, or fibroin from a silkworm.

The high-molecular polysaccharide may be used without limitation as long as it can be blended with cosmetics. Preferably, the high-molecular polysaccharide may include hydroxyethyl cellulose, xanthan gum, sodium hyaluronate, chondroitin sulphate or salts thereof (sodium salt, etc.). For example, chondroitin sulphate or a salt thereof may be generally purified from a mammal or a fish.

The sphingolipid may be used without limitation as long as it can be blended with cosmetics. Preferably, the sphingolipid may include ceramide, phytosphingosine, glycosphingolipid, etc. The sphingolipid may be generally purified from a mammal, a fish, a shellfish, yeast or a plant using a conventional method, or obtained using a conventional method such as chemical synthesis.

In addition to the essential components, the cosmetic composition of the present disclosure may include other components that may be blended into a conventional cosmetic composition, when necessary.

In addition to the above-described components, a blending component which may be added herein may include a fat component, a humectant, an emollient, a surfactant, organic and inorganic pigments, an organic powder, a UV absorber, an antiseptic, a bactericide, an antioxidant, an herbal extract, a pH adjusting agent, an alcohol, a colorant, an aromatic, a blood flow stimulant, a cooling agent, an antiperspirant, purified water, etc.

The fat component may include ester-based fat, hydrocarbon-based fat, silicon-based fat, fluorine-based fat, animal fat, vegetable fat, etc.

The ester-based fat may include tri-2-ethylhexaneglyceryl, 2-ethylhexanecetyl, myristic acid isopropyl, myristic acid butyl, palmitic acid isopropyl, stearic acid ethyl, palmitic acid octyl, isostearic acid isocetyl, stearic acid butyl, linoleic acid ethyl, linoleic acid isopropyl, oleic acid ethyl, myristic acid isocetyl, myristic acid isostearyl, palmitic acid isostearyl, myristic acid octyldodecyl, isostearic acid isocetyl, sebacic acid diethyl, adipic acid diisopropyl, neopentanoic acid isoalkyl, tri(caprylic, capric acid)glyceryl, tri-2-ethylhexanetrimethylolpropane, triisostearic acid trimethylolpropane, tetra-2-ethylhexanepentaerythritol, caprylic acid cetyl, lauric acid decyl, lauric acid hexyl, myristic acid decyl, myristic acid myristyl, myristic acid cetyl, stearic acid stearyl, oleic acid decyl, ricinoleic acid cetyl, lauric acid isostearyl, myristic acid isotridecyl, palmitic acid isocetyl, stearic acid octyl, stearic acid isocetyl, oleic acid isodecyl, oleic acid octyldodecyl, linoleic acid octyldodecyl, isostearic acid isopropyl, 2-ethyl hexanecetostearyl, 2-ethylhexanestearyl, isostearic acid hexyl, dioctanoic acid ethyleneglycol, dioleic acid ethyleneglycol, dicapric acid propylene glycol, di(caprylic, capric acid) propylene glycol, dicaprylic acid propylene glycol, dicapric acid neopentylglycol, dioctanoic acid neopentylglycol, tricaprylic acid glyceryl, triundecylic acid glyceryl, triisopalmitic acid glyceryl, triisostearic acid glyceryl, neopentanoic acid octyldodecyl, octanoic acid isostearyl, isononanoic acid octyl, neodecanoic acid hexyldecyl, neodecanoic acid octyldodecyl, isostearic acid isocetyl, isostearic acid isostearyl, isostearic acid octyldecyl, polyglycerineoleic acid ester, polyglycerineisostearic acid ester, citric acid triisocetyl, citric acid triisoalkyl, citric acid triisooctyl, lactic acid lauryl, lactic acid myristyl, lactic acid cetyl, lactic acid octyldecyl, citric acid triethyl, citric acid acetyltriethyl, citric acid acetyltributyl, citric acid trioctyl, malic acid diisostearyl, hydroxystearic acid 2-ethylhexyl, succinic acid di-2-ethylhexyl, adipic acid diisobutyl, sebacic acid diisopropyl, sebacic acid dioctyl, stearic acid cholesteryl, isostearic acid cholesteryl, hydroxystearic acid cholesteryl, oleic acid cholesteryl, oleic acid dihydrocholesteryl, isostearic acid phytosteryl, oleic acid phytosteryl, 12-stearoylhydroxystearic acid isocetyl, 12-stearoylhydroxystearic acid stearyl, 12-stearoylhydroxystearic acid isostearyl, etc.

The hydrocarbon-based fat may include squalene, liquid paraffin, α-olefin oligomer, isoparaffin, ceresin, paraffin, liquid isoparaffin, polybutene, microcrystalline wax, Vaseline, etc.

The silicon-based fat may include polymethylsilicon, methylphenylsilicon, methylcyclopolysiloxane, octamethylpolysiloxane, decamethylpolysiloxane, dodecamethylcyclosiloxane, a dimethylsiloxane/methylcetyloxysiloxane copolymer, a dimethylsiloxane/methylstearoxysiloxane copolymer, alkyl-modified silicon oil, amino-modified silicon oil, etc.

The fluorine-based fat may include perfluoropolyether, etc.

The animal or vegetable fat may include avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cottonseed oil, coconut oil, wheat germ oil, rice germ oil, shea butter, evening primrose oil, macadamia nut oil, meadowfoam oil, egg yolk oil, tallow, horse oil, mink oil, orange roughy oil, jojoba oil, candelilla wax, carnauba wax, liquid lanolin, hydrogenated castor oil, etc.

The humectant may include a water-soluble low-molecular humectant, a fat-soluble low-molecular humectant, a water-soluble polymer, a fat-soluble polymer, etc.

The water-soluble low-molecular humectant may include serine, glutamine, sorbitol, mannitol, pyrrolidone-sodium carboxylate, glycerine, propylene glycol, 1,3-butyleneglycol, ethyleneglycol, polyethyleneglycol B (degree of polymerization (n) of at least 2), polypropylene glycol (degree of polymerization (n) of at least 2), polyglycerine B (degree of polymerization (n) of at least 2), lactic acid, lactate, etc.

The fat-soluble low-molecular humectant may include cholesterol, cholesterolester, etc.

The water-soluble polymer may include carboxyvinyl polymer, polyaspartate, tragacanth, xanthan gum, methyl cellulose, hydroxymethylcellulose, hydroxyethyl cellulose, hydroxypropyl cellulose, carboxymethyl cellulose, water-soluble chitin, chitonic acid, dextrin, etc.

The fat-soluble polymer may include a polyvinylpyrrolidone/eicosene copolymer, a polyvinylpyrrolidone/hexadecene copolymer, nitrocellulose, dextrin fatty acid ester, polymer silicon, etc.

The emollient may include long-chain acyl glutamic acid cholesteryl ester, hydroxystearic acid cholesteryl, 12-hydroxystearic acid, stearic acid, rosin acid, lanolin fatty acid cholesteryl ester, etc.

The surfactant may include a non-ionic surfactant, an anionic surfactant, a cationic surfactant, an amphoteric surfactant, etc.

The non-ionic surfactant may include self-emulsified monostearic acid glycerine, propylene glycol fatty acid ester, glycerine fatty acid ester, polyglycerine fatty acid ester, sorbitan fatty acid ester, polyoxyethylene (POE) sorbitan fatty acid ester, POE sorbite fatty acid ester, POE glycerine fatty acid ester, POE alkylether, POE fatty acid ester, POE hydrogenated caster oil, POE castor oil, a POE/ polyoxypropylene (POP) copolymer, POE/POP alkylether, polyether-modified silicon, lauric acid alkanol amide, alkylamine oxide, hydrogenated soybean phospholipid, etc.

The anionic surfactant may include fatty acid soap, α-acylsulfonate, alkylsulfonate, alkylarylsulfonate, alkylnaphthalenesulfonate, alkylsulfate, POE alkylethersulfate, alkylamidesulfate, alkylphosphate, POE alkylphosphate, alkylamidephosphate, alkyloylalkyltaurate, N-acylamino acid salt, POE alkylethercarboxylate, alkylsulfosuccinate, sodiumalkylsulfoacetate, acylated hydrolyzed collagen peptide salt, perfluoroalkyl phosphate ester, etc.

The cationic surfactant may include alkyltrimethyl ammonium chloride, stearyltrimethyl ammonium chloride, stearyltrimethylammonium bromide, cetostearyltrimethyl ammonium chloride, distearyldimethyl ammonium chloride, stearyldimethylbenzyl ammonium chloride, behenyltrimethyl ammonium bromide, benzalkonium chloride, diethylaminoethylamide stearate, dimethylaminopropylamide stearate, quaternary ammonium derivatives of lanolin, etc.

The amphoteric surfactant may include carboxybetaine-type, amide betaine-type, sulfobetaine-type, hydroxyl sulfobetaine-type, amide sulfobetaine-type, phosphobetaine-type, aminocarboxylate-type, imidazoline derivative-type, amideamine-type amphoteric surfactants, etc.

The organic and inorganic pigment may include an inorganic pigment such as silicic acid, silica, magnesium silicate, talc, sericite, mica, kaolin, rouge, clay, bentonite, titan-coated mica, bismuth oxychloride, zirconium oxide, magnesium oxide, zinc oxide, titanium oxide, aluminium oxide, calcium sulfate, barium sulfate, magnesium sulfate, calcium carbonate, magnesium carbonate, iron oxide, ultramarine, chromium oxide, chromium hydroxide, calamine and a complex thereof; an organic pigment such as polyamide, polyester, polypropylene, polystyrene, polyurethane, vinyl resin, urea resin, phenol resin, fluorine resin, silica resin, acrylic resin, melamine resin, epoxy resin, polycarbonate resin, a divinylbenzene/styrene copolymer, silk powder, cellulose, CI Pigment Yellow, or CI Pigment Orange; and a complex pigment of the inorganic pigment and the organic pigment, etc.

The organic powder may include a metallic soap such as calcium stearate; a metal alkylphosphate such as zinc sodium cetylate, zinc laurylate or calcium laurylate; a polyvalent acylamino acid metal salt such as N-lauroyl-β-alanine calcium, N-lauroyl-β-alanine zinc or N-lauroyl glycine calcium; a polyvalent amide sulfonic acid metal salt such as N-lauroyl-taurine calcium or N-palmitoyl-taurine calcium; a N-acyl basic amino acid such as N-ε-lauroyl-L-lysine, N-ε-palmitoyllysine, N-α-palmitoyl ornithine, N-α-lauroylarginine, or N-α-hydrogenated tallow fatty acid acyl arginine; an N-acylpolypeptide such as N-lauroylglycylglycine, an α-amino fatty acid such as α-amino caprylic acid, or α-amino lauric acid; polyethylene, polypropylene, nylon, polymethylmethacrylate, polystyrene, divinylbenzene/styrene copolymer, tetrafluoroethylene, etc.

The UV absorber may include para-amino benzoic acid, ethyl-para-benzoate, amyl-para-aminobenzoate, octyl-para-aminobenzoate, salicylic acid ethylene glycol, henyl salicylate, octyl salicylate, benzyl salicylate, butylphenyl salicylate, homomentyl salicylate, benzyl cinnamate, 2-ethoxyethyl para-methoxy cinnamate, octyl para-methoxy cinnamate, mono-2-ethyl hexane glyceryl di-para-methoxy cinnamate, isopropyl para-methoxy cinnamate, a diisopropyl/diisopropyl cinnamic acid ester mixture, urocanic acid, ethyl urocanate, hydroxy methoxybenzophenone, hydroxyl methoxybenzophenone sulfonic acid and slats thereof, dihydroxy methoxybenzophenone, sodium dihydroxy methoxybenzophenone disulfonate, dihydroxy benzophenone, tetrahydroxy benzophenone, 4-tert-butyl-4'-methoxy dibenzoylmethane, 2,4,6-trianilino-p-(carbo-2'-ethylhexyl-1'-oxy)-1,3,5-triazine, 2-(2-hydroxy-5-methylphenyl)benzotriazole, etc.

The bactericide may include hinokitiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, photosensitizer 301, sodium mononitroguaiacol, undecylenic acid, etc.

The antioxidant may include butylhydroxy anisole, propyl gallate, erythorbic acid, etc.

The pH regulating agent may include citric acid, sodium citrate, malic acid, sodium malate, fumaric acid, sodium fumarate, succinic acid, sodium succinate, sodium hydroxide, disodium hydrogen phosphate, etc.

The alcohol may include a higher alcohol such as cetyl alcohol.

In addition, a blending component which may be added herein is not limited to the above-described components, and any component may be blended in such a range that the objects and effects of the present disclosure are not hindered. That is, the component may be preferably blended in a content of 0.01 to 5% by weight, and more preferably a content of 0.01 to 3% by weight, based on the total weight of the composition.

The cosmetic composition of the present disclosure may be prepared in the form of a solution, an emulsion or a viscous mixture.

In addition to the compound, the components included in the cosmetic composition of the present disclosure may further include components generally used for a cosmetic composition as active ingredients. For example, the cosmetic composition includes a conventional adjuvant and carrier, such as a stabilizing agent, a solubilizing agent, a vitamin, a pigment or an aromatic.

The cosmetic composition of the present disclosure may be prepared as any formulation which is generally prepared in the art, and examples of the formulation may include a milky lotion, a cream, a face lotion, a pack, a foundation lotion, a lotion, an essence, a hair care composition, etc.

In detail, the cosmetic composition of the present disclosure may include formulations of a skin lotion, a skin softener, a skin toner, an astringent, a lotion, a milk lotion, a moisturizing lotion, a nourishing lotion, a massage cream, a nourishing cream, a hand cream, a foundation cream, an essence, a nourishing essence, a pack, a soap, a cleansing foam, a cleansing lotion, a cleansing cream, a body lotion, a body cleanser, etc.

When the formulation of the present disclosure is in the form of a paste, cream or gel, usable examples of the carrier component may include an animal fiber, a vegetable fiber, a wax, paraffin, a starch, tragacanth, a cellulose derivative, polyethylene glycol, silicon, bentonite, silica, talc or zinc oxide.

When the formulation of the present disclosure is in the form of a powder or spray, usable examples of the carrier component may include lactose, talc, silica, aluminum hydroxide, calcium silicate or polyamide powder. Particularly when the formulation of the present disclosure is in the form of spray, the formulation may further include a propellent such as chlorofluorohydrocarbon, propane/butane or dimethylether.

When the formulation of the present disclosure is in the form of a solution or emulsion, usable examples of the carrier component may include a solvent, a solvating agent or an emulsifying agent. For example, the carrier component may include water, ethanol, isopropanol, ethyl carbonate, ethyl acetate, benzyl alcohol, benzyl benzoate, propylene glycol, 1,3-butylglycol oil, aliphatic glycerol ester, polyethylene glycol, or sorbitan fatty acid ester.

When the formulation of the present invention is in the form of a suspension, usable examples of the carrier component may include a liquid diluent such as water, ethanol or propylene glycol, a suspension such as ethoxylated isostearyl alcohol, polyoxyethylene sorbitol ester or polyoxyethylene sorbitan ester, microcrystalline cellulose, aluminum methahydroxide, bentonite, agar or tragacanth.

When the formulation of the present invention is in the form of a surfactant-containing cleanser, usable examples of the carrier component may include aliphatic alcohol sulfate, aliphatic alcohol ether sulfate, sulfosuccinic acid monoester, isethionate, imidazolium derivative, methyltaurate, sarcosinate, fatty acid amide ether sulfate, alkylamido betaine, aliphatic alcohol, fatty acid glyceride, fatty acid diethanolamide, a vegetable oil, a linolin derivative or ethoxylated glycerol fatty acid ester.

In addition, the present disclosure provides a pharmaceutical composition for treating and preventing skin diseases, comprising as an effective ingredient a pseudoceramide compound acquired by the manufacturing method and demonstrating a skin protecting function and moisture retaining capacity.

Examples of the skin disease include atopic dermatitis, dermatitis due to chapped skin, miliaria, erosion, frostbite, diaper rash, contact dermatitis, seborrheic dermatitis, lichen Vidal, nummular eczema, housewife's eczema, photosensitivity dermatitis, insect bites, pruritus cutaneous, prurigo, drug eruption, toxic erythema, psoriasis, parapsoriasis, Pustulosis palmoplantaris, lichen planus, lichen nitidus, pityriasis rubra pilaris, Gibert pityriasis rosea, erythroplakia, dermatitis exfoliativa, dicoid lupus erythematosus, systemic lupus erythematosus, pemphigus, bollous pemphigoid, dermatitis herpetiformis Duhring, alopecia greata, vitiligo vulgaris, sarcoidosis, cutaneous amyloidosys, keloids, hypertrophic scars, wounds, bed sores, cutaneous ulcers, and alopecia.

The pharmaceutical composition comprising the compound according to the present disclosure comprises 0.1 to 50 wt %, based on the total weight of the pharmaceutical composition.

The pharmaceutical composition comprising the compound according to the present disclosure may further comprise a carrier, an excipient and a diluent, which are generally used in preparing the pharmaceutical composition.

The compound according to the present disclosure may be pharmaceutically administered in the form of a pharmaceutically acceptable salt thereof, and may be used alone or in combination or appropriate set of other pharmaceutically active compounds.

The pharmaceutical composition comprising the compound according to the present disclosure may be formulated into an externally-applied preparation, such as powder, granule, pill, capsule, suspension, emulsion, syrup or aerosol, and a sterile injectable solution using a conventional method. Preferably, the pharmaceutical composition is provided in the form of a skin topical preparation, such as an ointment, a plaster, a lotion, a liniment, a paste or a cataplasma. Examples of the carrier, the excipient and the diluents, which can be included in the pharmaceutical composition comprising the compound according to the present disclosure, may include lactose, dextrose, sucrose, sorbitol, manitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate and mineral oil. When the pharmaceutical composition according to the present disclosure is formulated, a formulation may be prepared using a commonly used diluent or excipient such as a filler, an extending agent, a binder, a wetting agent, a disintegrating agent and a surfactant. A formulation for parenteral administration includes a sterile aqueous solution, a non-aqueous solvent, a suspension, an emulsion, a lyophilized formulation, and a suppository. Usable examples of the non-aqueous solvent and the suspension may include a vegetable oil such as propylene glycol, polyethylene glycol or olive oil, and an injectable ester such as ethyl oleate.

A desirable dose of the pharmaceutical composition of the present disclosure may be varied according to the condition and weight of a patient, the severity of a disease, the type of a drug, and the route and duration of administration, or be suitably selected by those skilled in the art. In order to achieve desirable effects, however, the compound of the present disclosure may be administered daily at a dose of 0.0001 to 100 mg/kg, and preferably 0.001 to 10 mg/kg. The administration may be performed once a day or in divided doses each day. Therefore, the dosage is not intended to limit the scope of the present disclosure in any aspect.

MODE OF DISCLOSURE

Hereinafter, the present disclosure will be described in detail through the following Examples and Experimental Examples. However, the following Examples are provided only for easily understanding the present disclosure as illustrative examples, but the scope of the present disclosure is not limited thereto.

To be compared with the activity of the pseudoceramide compound of the present disclosure, a compound of Formula 7 (Korean Patent No. 10-1641702) was used as Comparative Example.

[Formula 7]

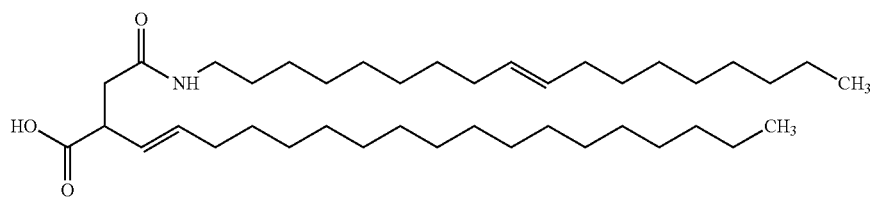

Synthesis Example 1: Synthesis of Novel Compound Having a Pseudoceramide Structure 5.02 g of 2-dodecenyl succinic anhydride represented by Formula 8 and 5.08 g of stearyl amine represented by Formula 9 were put into a 250 ml flask. Here, stearyl amine was used after being diluted in dichloromethane as a solvent. Thereafter, the resultant product was agitated for 30 minutes to allow a reaction to take place. As the result of the reaction, the pseudoceramide compound represented by Formula 3 (to be referred to as 'Formula 3' hereinafter) was obtained.

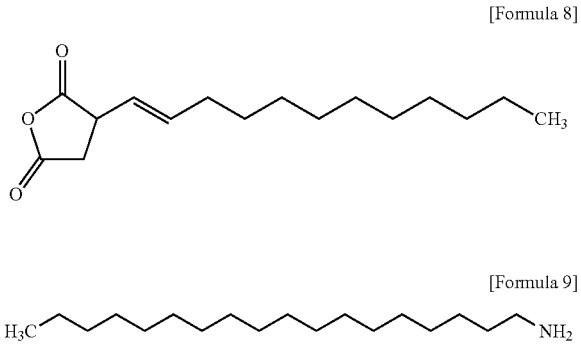

[Formula 8]

[Formula 9]

Example 1 and Comparative Examples 1-2: Preparation of Moisturizing Lotion

Moisturizing lotion formulations including the novel pseudoceramide compound of the present disclosure were prepared in Example 1 and Comparative Examples 1 and 2 using ingredients listed in Table 1 by a general method known in the art to which the present disclosure pertains.

TABLE 1

| | Ingredient (wt %) | Example 1 | Comparative Example 1 | Comparative Example 2 |
|---|---|---|---|---|
| A | Cetearath-20 | 3 | 3 | 3 |
| | Formula 3 | 0.5 | — | — |
| | Formula 7 | — | 0.5 | — |
| | Dimethicone | 1 | 1 | 1 |
| B | Distilled water | TO 100 | TO 100 | TO 100 |
| C | Glycerin | 5 | 5 | 5 |
| | Butylene glycol | 5 | 5 | 5 |
| | Mineral oil | 11 | 11 | 11 |
| | Carbomer | 0.1 | 0.1 | 0.1 |
| | Xanthan gum | 0.03 | 0.03 | 0.03 |

TABLE 1-continued

| | Ingredient (wt %) | Example 1 | Comparative Example 1 | Comparative Example 2 |
|---|---|---|---|---|
| D | Stearic acid | 1 | 1 | 1 |
| E | Potassium hydroxide | Qs. (quantum satis) | Qs. | Qs. |
| F | Aromatic | Qs. | Qs. | Qs. |
| G | Antiseptic | Qs. | Qs. | Qs. |

Experimental Example 1: Transepidermal Water Loss Recovery Capacity in Human Body Moisturizers of lotion formulations including the novel compounds having the pseudoceramide structure prepared in Example 1 and Comparative Examples 1 and 2 were evaluated in view of transepidermal water loss recovery capacity. The moisture retaining capacity of each moisturizer was tested in the following manner.

Tests for evaluating the transepidermal water loss recovery capacity were conducted on 8 healthy female and male persons at the age of 20-35 years as test subjects. The test area was the inward region of the arm of each person. The test area was washed away with running water before a moisturizer sample was topically applied thereto. Here, a product including a moisturizing component or a strong cleansing component will not be used. Moisture was gently removed from the test area and the test area was slowly dried for 20-30 minutes. As shown in FIG. 1, as many 2.0×2.0 cm rectangles as samples were marked on the test area (the upper arm). Before applying the sample, transepidermal water loss (TEWL) was measured 5 times using a vapometer, and an average of 3 measurements was obtained, excluding the minimum value and the maximum value. In order to induce acute skin barrier damages, tape stripping was repeatedly (about 30 times) performed on the same test area. After the acute skin barrier damages were induced, a predetermined amount of the sample was applied to the damaged area to then allow the sample to be sufficiently absorbed into the damaged area. The sample was applied to the same test area once a day, capacitance was measured before the skin damage was induced and 3, 6, 24, 30, and 48 hours after the skin damage was induced, and an average of the measurements was obtained.

The results are summarized in Table 2 below.

Table 2 shows mean values and of transepidermal water loss measurements.

Figure 2:
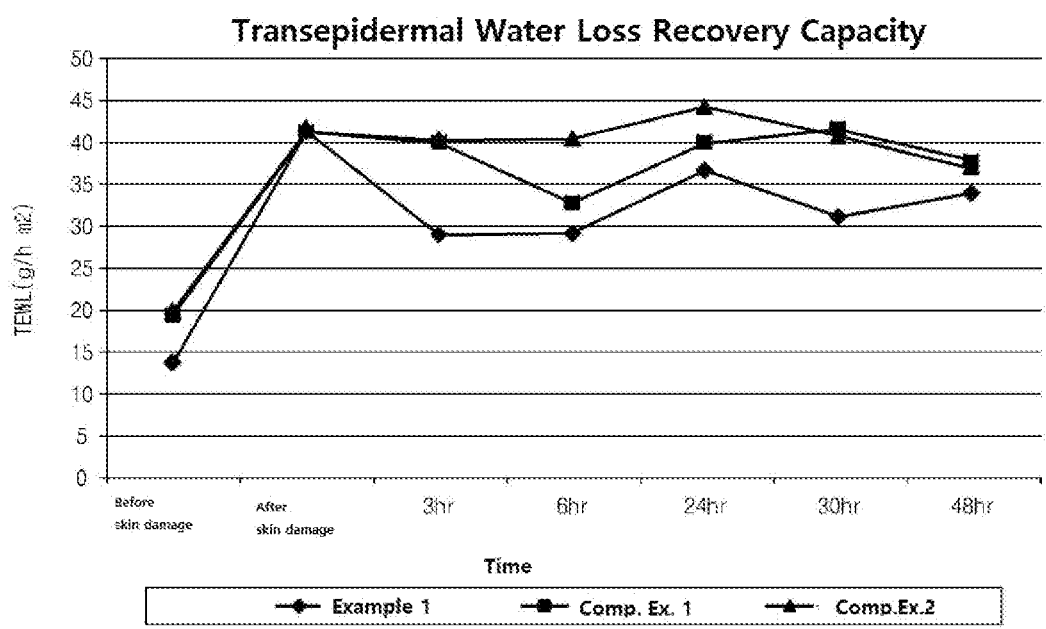
FIG. 2 illustrates changes in the transepidermal water loss according to Experimental Example 1 of the present disclosure.

FIG. 2 shows changes in transepidermal water loss measurements according to Experimental Example 1 of the present disclosure.

TABLE 2

| | Before skin damage | After skin damage | 3 hours | 6 hours | 24 hours | 30 hours | 48 hours |
|---|---|---|---|---|---|---|---|
| Example 1 | 19.87 | 41.10 | 40.10 | 40.37 | 44.20 | 40.70 | 37.07 |
| Comparative Example 1 | 19.20 | 41.00 | 39.93 | 32.60 | 39.80 | 41.40 | 37.63 |
| Comparative Example 2 | 13.70 | 40.90 | 29 | 29.17 | 36.53 | 30.97 | 33.90 |

Example 2 and Comparative Examples 3 and 4: Preparation of Moisturizing Creams

A formulation of a moisturizing cream including the novel pseudoceramide compound of the present disclosure (Example 2), a formulation of a moisturizing cream including commercially available conventional pseudoceramide compound PC-9S (U.S. Pat. No. 6,221,371) (Comparative Example 3), and a formulation of a moisturizing cream without a pseudoceramide compound (Comparative Example 4), were prepared using ingredients listed in Table 3 by a general method known in the art to which the present disclosure pertains.

TABLE 3

| | Ingredient (wt %) | Example 2 | Comparative Example 3 | Comparative Example 4 |
|---|---|---|---|---|
| A | Cetearath-20 | 3 | 3 | 3 |
| | Compound 3 | 0.3 | — | — |
| | PC-9S | — | 0.3 | — |
| | Dimethicone | 1 | 1 | 1 |
| B | Distilled water | TO 100 | TO 100 | TO 100 |
| C | Glycerin | 5 | 5 | 5 |
| | Butylene glycol | 5 | 5 | 5 |
| | Mineral oil | 11 | 11 | 11 |
| | Carbomer | 0.1 | 0.1 | 0.1 |
| | Xanthan gum | 0.03 | 0.03 | 0.03 |
| D | Stearic acid | 1 | 1 | 1 |
| E | Potassium hydroxide | Qs. (quantum satis) | Qs. | Qs. |
| F | Aromatic | Qs. | Qs. | Qs. |
| G | Antiseptic | Qs. | Qs. | Qs. |

Experimental Example 2: Effect of Improving Skin Moisture Retaining Capacity in Human Body Moisturizers formulated into lotions including the novel compound of the pseudoceramide prepared in Example 2, a moisturizer including a known pseudoceramide produced by other company in Comparative Example 3, and a moisturizer without pseudoceramide prepared in Comparative Example 4, were evaluated in view of moisture retaining capacity. The moisture retaining capacity of each moisturizer was tested in the following manner.

Tests for evaluating moisture retaining capacity improvement rates were conducted on 8 healthy female and male persons at the age of 20-35 years as test subjects. The test area was the inward region of the arm of each person. The test area was washed away with running water before a moisturizer sample was topically applied thereto. Here, a product including a moisturizing component or a strong cleansing component will not be used. Moisture was gently removed from the test area and the test area was slowly dried for 20-30 minutes. As shown in FIG. 1, as many 2.0×2.0 cm rectangles as samples were marked on the test area (the upper arm). Before applying the sample, capacitance was measured 5 times using a corneometer, and an average of 3 measurements was obtained, excluding the minimum value and the maximum value. The sample was applied to the same test area once a day, the capacitance was measured before applying the sample and 3, 5 and 8 hours after applying the sample, and an average of the measurements was obtained.

Figure 3:
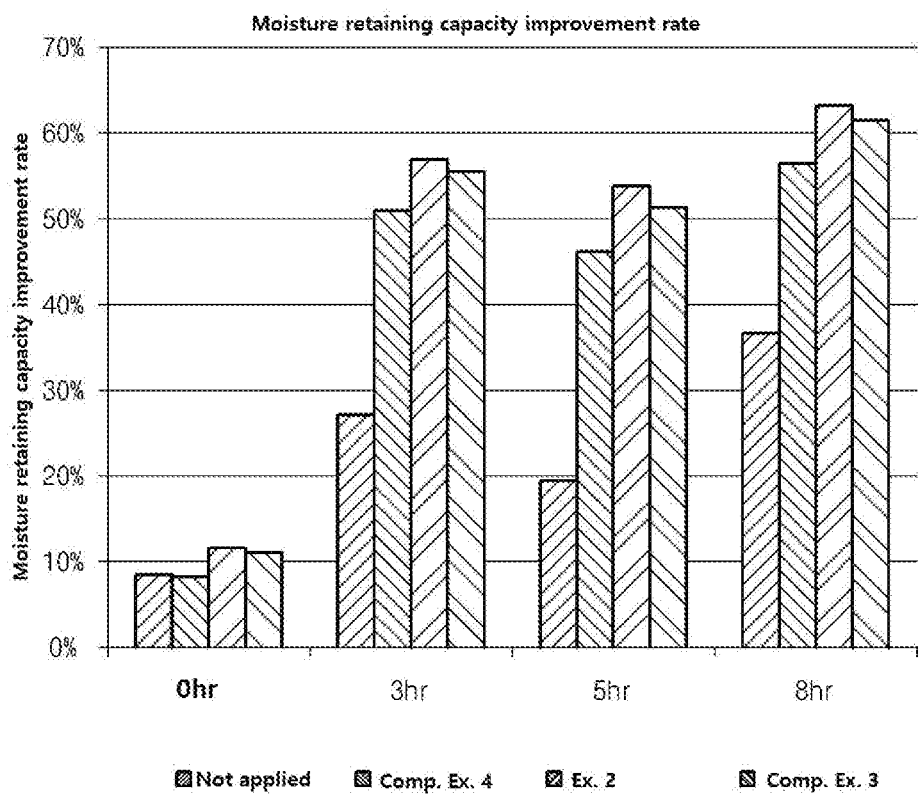
FIG. 3 illustrates changes of values in moisture retaining capacity according to Experimental Example 2, as measured using a corneometer.
Figure 4:
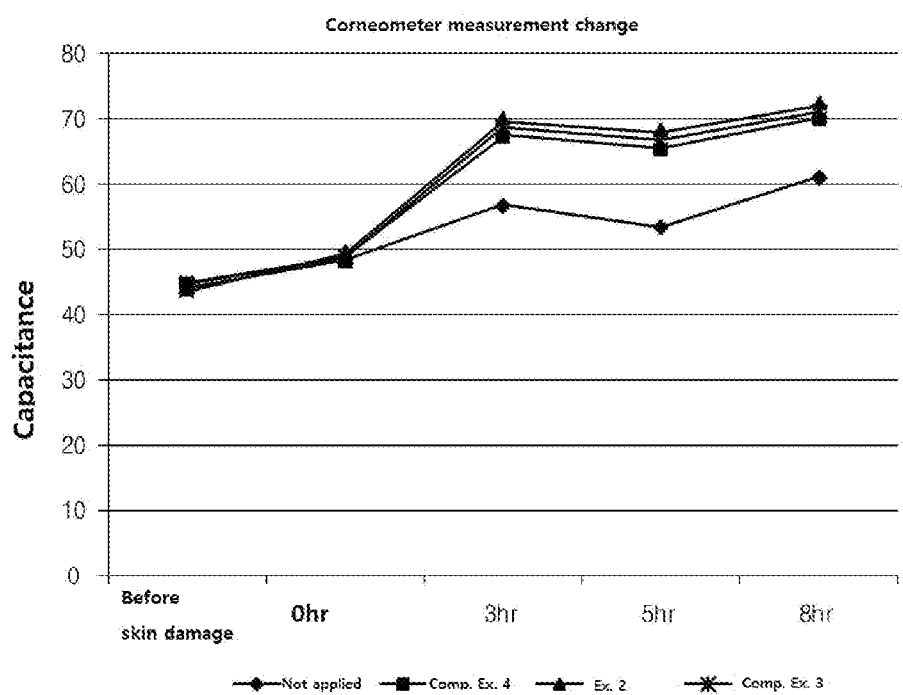
FIG. 4 illustrates moisture retaining capacity improvement rates according to Experimental Example 2.

The corneometer for measurement can measure any part of the body at 100 to 240V AC, 0.3 A, 50 to 60 Hz with measurable area 49 mm$^2$=3% accuracy. In addition, corneometer measurements can be obtained within a very short time, thereby facilitating repeated measurements. The test results are shown in FIGS. 3 and 4. The moisture retaining capacity improvement rate can be calculated using the following equation:

Moisture retaining improvement rate=[(average value per material−average value before applying sample)/average value before applying sample]× 100

The results are summarized in Table 4 below.

Table 4 shows mean values of corneometer measurements.

The results summarized in Table 5 are increased values measured after treatment for a predetermined time based on the corneometer measurements immediately before the start of experiments, as indicated in percentage.

FIG. 3 illustrates changes of values in moisture retaining capacity of a moisturizing lotion prepared in Experimental Example 2, as measured by a corneometer.

FIG. 4 illustrates moisture retaining capacity improvement rates of a moisturizing lotion prepared in Experimental Example 2.

TABLE 4

| | Before skin damage | After skin damage | 3 hours | 5 hours | 8 hours |
|---|---|---|---|---|---|
| Not applied | 44.65 | 48.46 | 56.77 | 53.32 | 61.04 |
| Comparative Example4 | 44.76 | 48.40 | 67.58 | 65.45 | 70.10 |
| Example 2 | 44.08 | 49.12 | 69.23 | 67.84 | 71.89 |
| Comparative Example3 | 43.92 | 48.75 | 68.33 | 66.40 | 70.95 |

TABLE 5

| | After skin damage | 3 hours | 5 hours | 8 hours |
|---|---|---|---|---|
| Not applied | 8.53 | 27.14 | 19.42 | 36.71 |
| Comparative Example 4 | 8.13 | 50.98 | 46.22 | 56.61 |
| Example 2 | 11.43 | 57.06 | 53.90 | 63.09 |
| Comparative Example3 | 11.00 | 55.58 | 51.18 | 61.54 |

Examples 3-4 and Comparative Examples 5 and 6: Preparation of Hair Essence

Formulations of hair essence including the novel pseudoceramide compounds of the present disclosure, and formulations of hair essence including conventional pseudoceramide compounds, were prepared in Examples 3-4 and Comparative Examples 5-6, respectively, using ingredients listed in Table 6 by a general method known in the art to which the present disclosure pertains.

TABLE 6

| Ingredient (wt %) | Example 3 | Example 4 | Comparative Example5 | Comparative Example6 |
|---|---|---|---|---|
| Distilled water | To 100 | To 100 | To 100 | To 100 |
| Compound 3 | 0.3 | 0.5 | — | — |
| Compound 7 | — | — | 0.5 | — |
| Dicaprylyl ether | 0.5 | 0.5 | 0.5 | 0.5 |
| Behentrimonium methosulfate | 0.5 | 0.5 | 0.5 | 0.5 |

TABLE 6-continued

| Ingredient (wt %) | Example 3 | Example 4 | Comparative Example5 | Comparative Example6 |
|---|---|---|---|---|
| Cetearyl alcohol | 6 | 6 | 6 | 6 |
| peroxyethanol | 0.5 | 0.5 | 0.5 | 0.5 |
| Cyclomethicone | 1 | 1 | 1 | 1 |
| Aromatic | Qs. | Qs. | Qs. | Qs. |

Experimental Example 3: Hair Tensile Strength Evaluation

To evaluate internal hair tissue damage treatment effects after using hair cosmetic compositions prepared in Examples and Experimental Examples, hair tensile strength tests were conducted, and the results are summarized in Table 7.

As a test for measuring the hair resistance against the force applied at a constant speed, if the hair is pulled by applying a force to the hair, the length of the hair is gradually increased, and the hair tensile strength is evaluated by the weight of the force applied to the hair until the hair breaks.

To conduct the experiment for a tensile strength test, 30 strands among Asian female virgin hair strands, purchased from De-Meo Brothers Co. (US), were cut, and 20 strands having similar thicknesses were then selected.

After treating the damaged hair (bleached twice) with the hair cosmetic compositions prepared in Examples, the force applied until the hair breaks was measured using a Dia-Stron tester, and hair breakage improvement rates of damaged hair strands relative the average value were calculated.

The Dia-Stron tester used for measuring the tensile strengths was a miniature tensile tester (Dia-Stron Limited, MTT175).

Table 7 indicates average values of tensile strength measurements (Dia-Stron Limited, MTT175 Miniature Tensile Tester).

The results indicated in Table 8 are calculation data of average hair breakage improvement rates of the damaged hair strands by measuring the force taken until the hair breaks using the Dia-Stron tester after treating the damaged hair with the hair cosmetic compositions prepared in Examples stated above.

Figure 5:
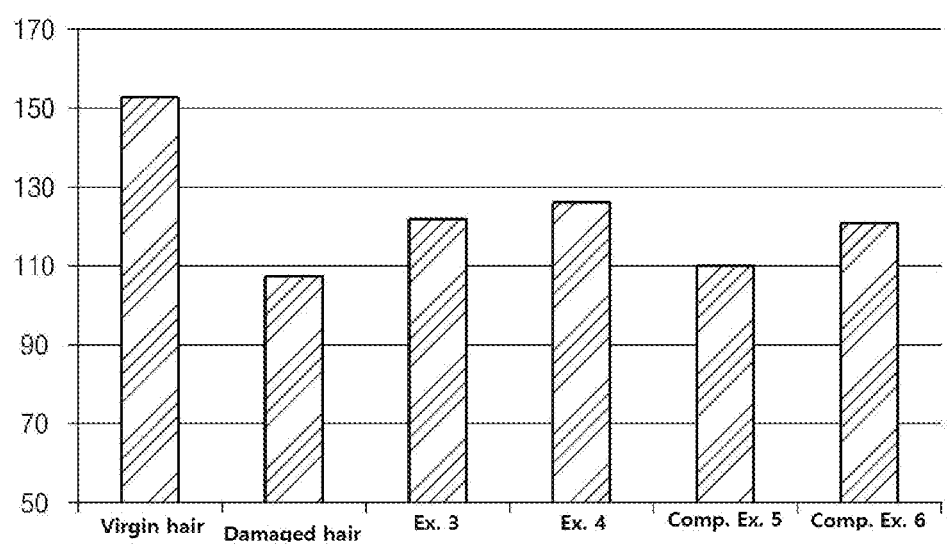
FIG. 5 illustrates changes of values in tensile strength according to Experimental Example 3, as measured using a tensile tester (Dia-Stron Limited, MTT175 Miniature Tensile Tester).

FIG. 5 illustrates changes of tensile strength measurements in Experimental Example 3, as measured by a miniature tensile tester (Dia-Stron Limited, MTT175).

TABLE 7

|  | Virgin hair | Damaged hair | Example 3 | Example 4 | Comparative Example 5 | Comparative Example 6 |
|---|---|---|---|---|---|---|
| Tensile strength (gmf) | 152.5 | 107.3 | 122 | 126 | 110 | 121 |

TABLE 8

| Evaluation item | Example 3 | Example 4 | Comparative Example5 | Comparative Example6 |
|---|---|---|---|---|
| Damaged hair improvement rate (%) | 13.2% | 17.4% | 12.5% | 12.7% |

As confirmed from Experimental Examples 1 to 3, the comparative evaluation results demonstrated that the compound of Formula 3 was equal to or higher than the compound of Formula 7 in view of performance.

In addition, as indicated in Table 9, thermal stability experiments were conducted through HPLC analysis, and the results showed that the compound of Formula 3 exhibited better high-temperature stability than the compound of Formula 7. The thermal stability tests were conducted by heating the compound samples of Formulas 3 and 7 in an oven maintained at 90° C. and measuring the degree of decomposition of each sample. When changes in the peak areas of the samples were compared, the compound of Formula 3 exhibited little change in the peak area ratio at 90° C. even after 24 hours, while the compound of Formula 7 showed a considerable degree of decomposition, that is, the peak area after 24 hours was nearly one third of the initial peak area.

TABLE 9

| Formula 3 | | Formula 7 | |
|---|---|---|---|
| Time | Peak area | Time | Peak area |
| 0 hour | 22760548 | 0 hour | 21694395 |
| 1 hour | 22871539 | 3 hours | 10982003 |
|  |  | 6 hours | 11400622 |
| 24 hours | 22896857 | 24 hours | 7124834 |

Compared to the conventional pseudoceramide compound of Formula 7 (Korean Patent No. 10-1641702), the novel pseudoceramide compound represented by Formula 3, according to the present disclosure had improved stability and better performance on skin and hair.

Example 5: Ointment Composition (Preparation Example of Pharmaceutical Composition)

An ointment composition including the novel pseudoceramide compound according to the present disclosure was prepared using ingredients listed in Table 10 by a general method known in the art to which the present disclosure pertains.

TABLE 10

| Function | Ingredient | Content (%) |
|---|---|---|
| A | Chia seed oil | 4.0 |
|  | Formula 3 | 1.0 |
|  | Petrolatum | Qs. |
|  | Cetostearyl alcohol | 3.0 |
|  | Hard liquid paraffin | 5.0 |
|  | Tocopheryl acetate | 2.0 |
|  | Ceteareth-20 | 3.0 |

TABLE 10-continued

| Function | Ingredient | Content (%) |
|---|---|---|
| B | Panthenol | 0.5 |
|  | Distilled water | Balance |
| C | Methyl p-hydroxybenzoate | Qs. |
|  | Propyl p-hydroxybenzoate | Qs. |

The invention claimed is:

1. A novel pseudoceramide compound represented by Formula 2:

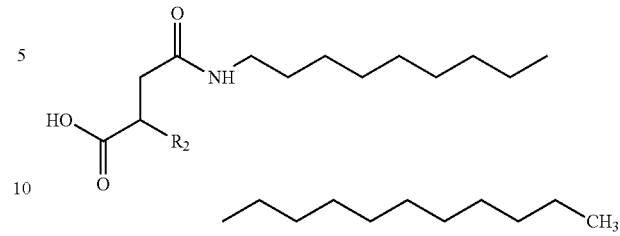

[Formula 2]

wherein $R_2$ represents an unsaturated linear C4-C22 alkyl group and has only one double bond.

2. The novel pseudoceramide compound of claim 1, which is represented by one of Formulas 3 to 6:

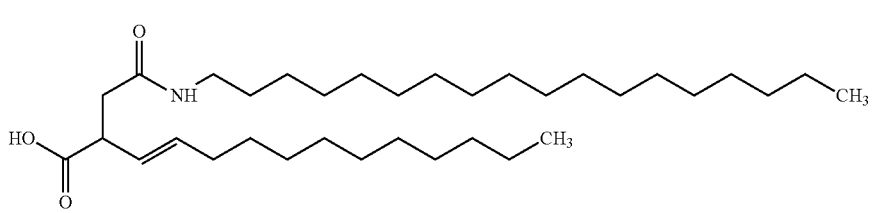

[Formula 3]

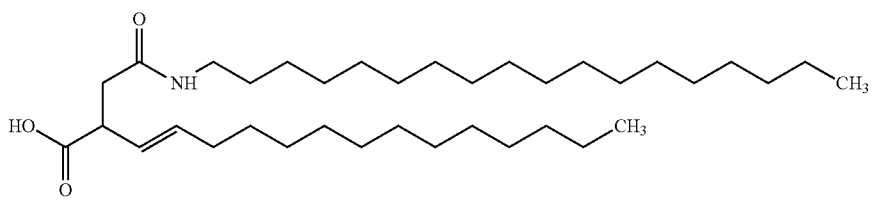

[Formula 4]

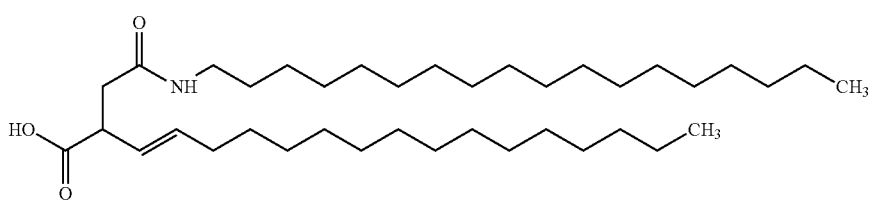

[Formula 5]

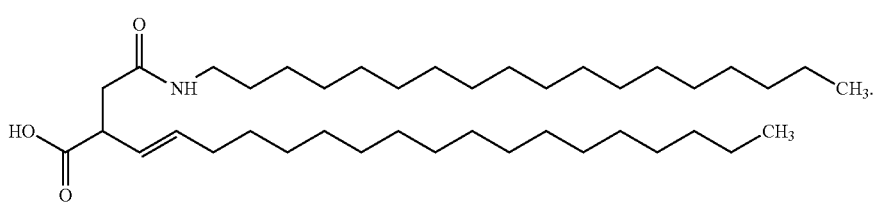

[Formula 6]

3. A skin-moisturizing cosmetic composition comprising the novel pseudoceramide compound of claim 1.

4. The skin-moisturizing cosmetic composition of claim 3, which is formulated into one or more selected from the group consisting of a cream, an essence, a lotion, a toner, a gel, and an ointment.

5. A hair cosmetic composition comprising the novel pseudoceramide compound of claim 1.

6. A skin-moisturizing externally-applied dermal preparation composition comprising the novel pseudoceramide compound of claim 1.

7. A skin-moisturizing cosmetic composition comprising the novel pseudoceramide compound of claim 2.

8. A hair cosmetic composition comprising the novel pseudoceramide compound of claim 2.

9. A skin-moisturizing externally-applied dermal preparation composition comprising the novel pseudoceramide compound of claim 2.

* * * * *